United States Patent
Aduri et al.

(10) Patent No.: US 9,238,611 B2
(45) Date of Patent: Jan. 19, 2016

(54) PROCESS FOR SEPARATING ARYL CARBOXYLIC ACIDS

(71) Applicant: Reliance Industries Limited, Mumbai, Maharashtra (IN)

(72) Inventors: Pavankumar Aduri, Maharashtra (IN); Parasu Veera Uppara, Maharashtra (IN); Suresh Shantilal Jain, Maharashtra (IN); Uday Ratnaparkhi, Maharashtra (IN)

(73) Assignee: Reliance Industries Limited, Mumbai, Maharashtra (IN)

( * ) Notice: Subject to any disclaimer, the term of this patent is extended or adjusted under 35 U.S.C. 154(b) by 0 days.

(21) Appl. No.: 14/387,652

(22) PCT Filed: Mar. 25, 2013

(86) PCT No.: PCT/IN2013/000195
§ 371 (c)(1),
(2) Date: Sep. 24, 2014

(87) PCT Pub. No.: WO2013/164852
PCT Pub. Date: Nov. 7, 2013

(65) Prior Publication Data
US 2015/0065748 A1    Mar. 5, 2015

(30) Foreign Application Priority Data
Mar. 27, 2012 (IN) .......................... 850/MUM/2012

(51) Int. Cl.
*C07C 51/43* (2006.01)
*C07C 51/42* (2006.01)

(52) U.S. Cl.
CPC ...................................... *C07C 51/43* (2013.01)

(58) Field of Classification Search
None
See application file for complete search history.

(56) References Cited

U.S. PATENT DOCUMENTS

| 2010/0174111 A1 | 7/2010 | Rogers et al. |
| 2012/0004456 A1 | 1/2012 | Bhattacharyya |

OTHER PUBLICATIONS

International Search Report of PCT/CN2013/000195 mailed Oct. 16, 2013.

*Primary Examiner* — Yevegeny Valenrod
(74) *Attorney, Agent, or Firm* — Collard & Roe, P.C.

(57) ABSTRACT

In the present disclosure, a process for separating aryl carboxylic acids from a mixture comprising a plurality of aryl carboxylic acids is provided, wherein the process comprising the steps of heating a first mixture that comprises at least two aryl carboxylic acids wherein each of said aryl carboxylic acids having a pre-determined liquefaction temperature and a pre-determined precipitation temperature, with at least one ionic compound, at a pre-determined temperature to obtain a liquefied composition; and cooling the liquefied composition under controlled temperature conditions to fractionally crystallize and precipitate an aryl carboxylic acid. The precipitated aryl carboxylic acid is isolated and the obtained mother liquor is subjected to iterated cooling steps until each of the remaining aryl carboxylic acids precipitates one by one. The mother liquor remains in liquefied form.

19 Claims, No Drawings

PROCESS FOR SEPARATING ARYL CARBOXYLIC ACIDS

CROSS REFERENCE TO RELATED APPLICATIONS

This application is the National Stage of PCT/IN2013/000195 filed on Mar. 25, 2013, which claims priority under 35 U.S.C. §119 of Indian Application No. 850/MUM/2012 filed on Mar. 27, 2012, the disclosures of which are incorporated by reference.

FIELD OF THE DISCLOSURE

The present disclosure relates to a process for separating aryl carboxylic acids from a mixture comprising a plurality of aryl carboxylic acids.

BACKGROUND

Terephthalic acid is an organic compound with formula $C_6H_4(COOH)_2$. This colourless solid is a commodity chemical, used principally as a precursor to the polyester PET, used to make clothing and plastic bottles. World production in 1970 was around 1.75 million tons. By 2006, the global demand for purified terephthalic acid (PTA) had exceeded 30 million tons. There is a smaller, but nevertheless significant, demand for terephthalic acid in the production of polybutylene terephthalate and several other engineering polymers. In the research laboratory, terephthalic acid is popularized as a component for the synthesis of metal-organic frameworks. The analgesic drug oxycodone occasionally comes as a terephthalate salt; however, the more usual salt of oxycodone is the hydrochloride. Pharmacologically, one milligram of terephthalas oxycodonae is equivalent to 1.13 mg of hydrochloridum oxycodonae. Terephthalic acid is also used as a filler in some military smoke grenades, most notably the American M83 smoke grenade, producing a thick white smoke when burned. Due to its wide applications, many methods for its manufacturing and purification are disclosed.

Conventionally, terephthalic acid is produced by the wet oxidation of para-xylene in acetic acid medium using cobalt and manganese acetates as a catalyst and hydrogen bromide as a promoter. However, along with the main oxidized product, for example terephthalic acid, various other intermediates and side products are also formed during the manufacturing thereof. These intermediates and side-products remain soluble during the reaction for complete conversion. The terephthalic acid thus produced by the wet oxidation of para-xylene traps some of the intermediates such as 4-carboxybenzaldehyde (4-CBA).

However, in order to use terephthalic acid as a starting material, for example, for the preparation of polyethylene terephthalate, the content of 4-CBA is recommended preferably below 100 ppm. Therefore, reducing 4-CBA impurity, particularly up to 25 ppm, is very important for further use of terephthalic acid. 4-CBA, if it exists in large quantities in terephthalic acid, acts as a chain terminator during the PET polymerization process, and hence desired PET molecular weight may not be achieved. Conventionally, crude terephthalic acid is subjected to hydrogenation to convert 4-carboxybenzaldehyde into p-toluic acid and subsequently p-toluic acid is separated.

Existing Knowledge:

US20100174111 discloses the use of imidazolium chloride ionic liquid for separating terephthalic acid and to deal with the removal of 4-carboxybenzaldehyde (4-CBA) as an impurity. However, the aforementioned patent application does not disclose reduction in impurity after reconstituting terephthalic acid in stages, though there is a mention of a stage wise process for reducing the impurity.

Further, US20120004456 discloses the use of solution comprising mixture of imidazolium based ionic liquids with solvent including water, carboxylic acid, and alcohol for the separation of terephthalic acid. Although, the use of ionic liquids as well as molecular solvents particularly alcohols is disclosed for the separation of terephthalic acid in the above cited documents, removal of various intermediates and side products that are formed during the manufacturing of terephthalic acid is not disclosed in the aforementioned US patent application. Also these disclosures use ionic liquids as solvents and use excess quantity to dissolve terephthalic acid, thereby increasing the cost of the process.

There is, therefore, a long felt need to provide a simple, safe and an economic process for separating aryl carboxylic acids which considerably consumes less time and requires optimal amount of solvents as compared to the prior-art processes wherein the solvent is usually employed in bulk quantities.

Objects:

Some of the objects of the present disclosure are as follows:

It is an object of the present disclosure to ameliorate one or more problems of the prior art or to at least provide a useful alternative.

Another object of the present disclosure is to provide a process for separating aryl carboxylic acids from a mixture comprising plurality of aryl carboxylic acids, intermediates and side products using ionic compounds.

Still another object of the present disclosure is to provide an ionic compound employed for the separation of aryl carboxylic acids.

A yet another object of the present disclosure is to provide an ionic compound employed as a solvent for the separation of aryl carboxylic acids.

Further object of the present disclosure is to provide an ionic compound employed as a solvent for the separation of aryl carboxylic acids from a mixture comprising plurality of aryl carboxylic acids, intermediates and side products, wherein the concentration of the intermediate products, particularly 4-carboxybenzaldehyde is reduced below desired ppm level.

Still further object of the present disclosure is to provide a simple, safe, efficient and economic process for separating aryl carboxylic acids.

Other objects and advantages of the present invention will be more apparent from the following description, which are not intended to limit the scope of the present invention.

Definitions

As used herein the term "liquefaction temperature" in the context of the present disclosure refers to a temperature at which a clear liquefied composition is obtained by heating together an ionic compound and an aryl carboxylic acid.

As used herein the term "precipitation temperature" in the context of the present disclosure refers to a temperature at which pure crystals of least soluble aryl carboxylic acid separates from a clear liquefied composition which is obtained by heating together an ionic compound and aryl carboxylic acid at a pre-determined liquefaction temperature of said aryl carboxylic acid.

SUMMARY

In accordance with the present disclosure there is provided a process for separating aryl carboxylic acids from a mixture comprising a plurality of aryl carboxylic acids, said process comprising the following steps:

i. providing a first mixture comprising at least two aryl carboxylic acids, each of said aryl carboxylic acids having a pre-determined liquefaction temperature and a pre-determined precipitation temperature;

ii. admixing said first mixture with at least one ionic compound to obtain a resultant mixture;

iii. subjecting the resultant mixture to a first pre-determined temperature until the first mixture completely liquefies along with the ionic compound to obtain a liquefied composition;

iv. subjecting said liquefied composition to a second pre-determined temperature to fractionally precipitate an aryl carboxylic acid, wherein said second pre-determined temperature is lower than the first pre-determined temperature;

v. isolating said precipitated aryl carboxylic acid from the liquefied composition and collecting the mother liquor; and vi. iterating the method step of subjecting to a second pre-determined temperature to further precipitate each of the remaining aryl carboxylic acids one by one from the mother liquor while retaining the mother liquor in liquefied form.

Typically, the first pre-determined temperature is the pre-determined liquefaction temperature of the aryl carboxylic acid.

Typically, the second pre-determined temperature is the pre-determined precipitation temperature of the aryl carboxylic acid.

Typically, the first pre-determined temperature varies between 20° C. to 300° C.

Typically, the second pre-determined temperature varies between 30° C. and 200° C., preferably between 80° C. and 120° C.

Typically, the first mixture comprises at least two of said aryl carboxylic acids in a total amount varying between 50 to 99.999% by weight, with respect to the total weight of the first mixture.

Typically, at least two of said aryl carboxylic acids are selected from the group consisting of terephthalic acid, isophthalic acid, orthophthalic acid, benzoic acid, p-toluic acid, m-toluic acid, o-toluic acid, 4-formyl benzoic acid, 3-formyl benzoic acid, 2-formyl benzoic acid, Naphthenic acid, Naphthoic acid, Trimesic acid, 3-Bromo, 4-methyl benzoic acid, 3-Hydroxy, 4-methyl benzoic acid, Trimellitic acid, mellitic acid 4-methyl phthalic acid, 2-Biphenyl carboxylic acid, Hemimellitic acid, 4-Bromo methyl benzoic acid and substituted benzoic acid.

Typically, the first mixture further comprises at least one intermediate product selected from the group consisting of 4-carboxybenzaldehyde, para-toluic acid and para-toulaldehyde.

Preferably, the first mixture comprises terephthalic acid and 4-carboxybenzaldehyde.

Typically, said at least one intermediate product is 4-carboxybenzaldehdye present in an amount ranging between 0.001% and 50% by weight, with respect to the total weight of the first mixture.

Typically, the ionic compound is at least one selected from the group of ionic compounds consisting of choline chloride, choline bromide, choline acetate, choline methane sulfonate, choline mesylate 1-butyl, 3-methyl imidazolium chloride, 1-butyl, 3-methyl imidazolium bromide, 1-butyl, 3-methyl imidazolium acetate, 1-butyl, 3-methyl imidazolium methane sulfonate, 1-butyl, 3-methyl imidazolium phosphate, 1-ethyl, 3-methyl imidazolium chloride, 1-ethyl, 3-methyl imidazolium bromide, 1-ethyl, 3-methyl imidazolium acetate, 1-ethyl, 3-methyl imidazolium methane sulfonate, 1-ethyl, 3-methyl imidazolium phosphate, 1-benzyl, 3-methyl imidazolium chloride, 1-benzyl, 3-methyl imidazolium bromide, 1-benzyl, 3-methyl imidazolium acetate, 1-benzyl, 3-methyl imidazolium methane sulfonate, 1-benzyl, 3-methyl imidazolium phosphate, Tetrabutyl phosphonium chloride, Tetrabutyl phosphonium bromide, Tetrabutyl phosphonium acetate, Tetrabutyl phosphonium methane sulfonate, Tetrabutyl phosphonium phosphate, Trihexyl Tetradecyl phosphonium chloride, Trihexyl Tetradecyl phosphonium bromide, Trihexyl Tetradecyl phosphonium acetate, Trihexyl Tetradecyl phosphonium decanoate, Benzyl tributyl phosphonium bromide, Tetrabutyl ammonium chloride, Tetrabutyl ammonium bromide, Tetrabutyl ammonium acetate, Tetrabutyl ammonium methane sulfonate, Tetrabutyl ammonium phosphate and Benzyl tributyl ammonium bromide.

Typically, the ionic compound and the first mixture are admixed in a weight proportion, expressed in terms of mole ratio, varying between 6:1 and 1:1, preferably between 3:1 and 1:1.

Preferably, the weight proportion of the ionic compound and the first mixture, expressed in terms of mole ratio, is 1:1.

Typically, the process in accordance with the present disclosure further comprising a method step of adding at least one solvent; said solvent being a miscible solvent with at least one of said first mixture, said ionic compound and said resultant mixture.

Typically, the solvent is at least one solvent selected from the group of solvents consisting of water, aliphatic alcohols, aromatic alcohols and carboxylic acids.

Preferably, the solvent is at least one solvent selected from the group of solvents consisting of benzyl alcohol, substituted benzyl alcohol, phenethyl alcohol, phenyl propyl alcohol, n-octanol, benzaldehyde, benzyl acetate, cetyl alcohol, fatty alcohols, phenol, substituted phenols and $C_8$-$C_{20}$ alcohols.

More preferably, the solvent is at least one substituted benzyl alcohol selected from the group consisting of 2-methylbenzyl alcohol, 4-chloro-2-methylbenzyl alcohol, 5-fluoro-2-methylbenzyl alcohol, o-fluorobenzyl alcohol, o-chlorobenzyl alcohol, o-bromobenzyl alcohol, o-iodobenzyl alcohol and o-nitrobenzyl alcohol.

Still more preferably, the solvent is benzyl alcohol.

Typically, the solvent is added during both the method step (iii) and the method step (iv) in accordance with the process of the present disclosure in a total amount varying between 25 to 0.0001 w/v.

Typically, the mother liquor comprises 4-carboxybenzaldehyde in completely dissolved form in the presence of said at least one miscible solvent.

Typically, the amount of 4-carboxybenzaldehyde in said precipitated aryl carboxylic acid is reduced up to 99.9%, with respect to its amount in the first mixture.

DETAILED DESCRIPTION

Accordingly, a process for separating aryl carboxylic acids from a mixture comprising a plurality of aryl carboxylic acids is provided in the present disclosure wherein major drawbacks identified in the aforementioned prior-arts are successfully circumvented by employing a very simple, safe, effective and economic process.

The process for separating aryl carboxylic acids from a mixture comprising a plurality of aryl carboxylic acids, in accordance with the present disclosure, comprising the steps of (i) providing a first mixture comprising at least two aryl carboxylic acids wherein each of said aryl carboxylic acids having a pre-determined liquefaction temperature and a pre-determined precipitation temperature; (ii) admixing the first mixture with at least one ionic compound to obtain a resultant mixture; (iii) subjecting the resultant mixture to a first pre-determined temperature until the first mixture completely liquefies along with the ionic compound to obtain a liquefied composition; and (iv) subjecting the liquefied composition to a second pre-determined temperature to fractionally precipitate an aryl carboxylic acid.

The first mixture as provided for the purpose of the present disclosure is a crude mixture that comprises at least two aryl carboxylic acids selected from the group consisting of terephthalic acid, isophthalic acid, orthophthalic acid, benzoic acid, p-toluic acid, m-toluic acid, o-toluic acid, 4-formyl benzoic acid, 3-formyl benzoic acid, 2-formyl benzoic acid, Naphthenic acid, Naphthoic acid, Trimesic acid, 3-Bromo, 4-methyl benzoic acid, 3-Hydroxy, 4-methyl benzoic acid, Trimellitic acid, mellitic acid 4-methyl phthalic acid, 2-Biphenyl corboxylic acid, Hemimellitic acid, 4-Bromo methyl benzoic acid, and substituted benzoic acid. Each of the aryl carboxylic acids is characterized with different liquefaction temperatures and different precipitation temperatures.

The first mixture comprising the at least two aryl carboxylic acids in accordance with the process of the present disclosure is an oxidative product of para-xylene. Since, the oxidative conversion of para-xylene to terephthalic acid is not 100%, therefore, in addition to the terephthalic acid which is formed as a main oxidized product, other products such as aryl carboxylic acids other than the terephthalic acid, and various intermediate and side products are also detected in the first mixture.

The intermediate product present in the first mixture of the present disclosure is at least one selected from the group consisting of para-tolualdehyde, para-toluic acid and 4-carboxybenzaldehyde.

In addition to above described intermediate products, the side products, for example, isophthalic acid, phthalic acid, meta or ortho-tolualdehyde, meta or ortho-toluic acid, 2 or 3-carboxybenzhaldehyde, 3 or 4-bromo methyl benzoic acid, benzoic acid, trimellitic acids, trimesic acid, benzaldehyde, phthalaldehyde, ethylbenzaldehyde, methylstyrene, diphenic acid, 2-biphenyl carboxylic acid, hemi melitic acid, dimethyl terephthalate, methyl p-toulate, 3-hydroxy 4-methyl benzoic acid, terephthal aldehyde, styrene, phenol, toluene, benzene, ethylbenzene, methylethylbenzene, formaldehyde, 1,3-cyclopentadiene, indene, methylnaphthalene, anthracene, phenantrene, phenylacetylene, methylbiphenyl, diphenylbutane, naphthalene, 4,4-dimethylbibenzyl and vinylacetylene are also detected in the first mixture. The first mixture comprises significantly lesser amount of side products as compared to the intermediate products.

The first mixture, in accordance with the process of the present disclosure, comprises the at least two aryl carboxylic acids in a total amount ranging between 50% and 99.999% by weight, with respect to the total weight of the first mixture; and at least one of said intermediate products in an amount ranging between 0.001% and 50% by weight, with respect to the total weight of the first mixture. The preferred intermediate product in accordance with the present disclosure is 4-carboxybenzaldehyde.

In accordance with one of the preferred embodiments of the present disclosure, the first mixture comprises terephthalic acid and 4-carboxybenzaldehyde.

The first mixture in accordance with the process of the present disclosure is then admixed with at least one ionic compound at a pre-determined temperature to obtain a resultant mixture. Preferably, the mixing is accomplished at ambient temperature.

The ionic compound suitable for the purpose of the present disclosure is a combination of at least one cationic species and at least one anionic species.

The preferred examples of cationic species, in accordance with the process of the present disclosure, include at least one selected from the group consisting of quaternary ammonium, cholinium, sulfonium, phosphonium, guanidinium, imidazolium, pyridinium, pyrrolidinium, morpholinium, quinolinium, isoquinolium, pyrazolium and piperidinium.

The preferred examples of anionic species, in accordance with the process of the present disclosure, includes at least one selected from the group consisting of halides, oxoanions, anions of organic acids, bicarbonates, hydroxide and oxides. The suitable examples of oxoanions for use as a cationic species includes at least one selected from the group consisting of mesylate, tosylate, hydrogen sulfate, sulfate, alkyl sulfonate, phosphates, phosphonates, alkyl phosphates, nitrates, nitrites, and carbonates.

In accordance with one of the preferred embodiments of the present disclosure, the ionic compound is at least one selected from the group consisting of choline chloride, choline bromide, choline acetate, choline methane sulfonate, choline mesylate 1-butyl, 3-methyl imidazolium chloride, 1-butyl, 3-methyl imidazolium bromide, 1-butyl, 3-methyl imidazolium acetate, 1-butyl, 3-methyl imidazolium methane sulfonate, 1-butyl, 3-methyl imidazolium phosphate, 1-ethyl, 3-methyl imidazolium chloride, 1-ethyl, 3-methyl imidazolium bromide, 1-ethyl, 3-methyl imidazolium acetate, 1-ethyl, 3-methyl imidazolium methane sulfonate, 1-ethyl, 3-methyl imidazolium phosphate, 1-benzyl, 3-methyl imidazolium chloride, 1-benzyl, 3-methyl imidazolium bromide, 1-benzyl, 3-methyl imidazolium acetate, 1-benzyl, 3-methyl imidazolium methane sulfonate, 1-benzyl, 3-methyl imidazolium phosphate, Tetrabutyl phosphonium chloride, Tetrabutyl phosphonium bromide, Tetrabutyl phosphonium acetate, Tetrabutyl phosphonium methane sulfonate, Tetrabutyl phosphonium phosphate, Trihexyl Tetradecyl phosphonium chloride, Trihexyl Tetradecyl phosphonium bromide, Trihexyl Tetradecyl phosphonium acetate, Trihexyl Tetradecyl phosphonium decanoate, Benzyl tributyl phosphonium bromide, Tetrabutyl ammonium chloride, Tetrabutyl ammonium bromide, Tetrabutyl ammonium acetate, Tetrabutyl ammonium methane sulfonate, Tetrabutyl ammonium phosphate and Benzyl tributyl ammonium bromide.

The weight proportion of the ionic compound and the first mixture, expressed in terms of mole ratio, typically varies between 6:1 and 1:1, preferably between 3:1 and 1:1. The ionic compound is preferably used in optimal amount. The preferred weight proportion of the ionic compound and the first mixture, expressed in terms of mole ratio, is 1:1.

The obtained resultant mixture is then subjected to a first pre-determined temperature until the first mixture completely liquefies along with the ionic compound to obtain a liquefied composition. Subjecting the resultant mixture to the first pre-determined temperature typically involves a method step of heating the resultant mixture at the first pre-determined temperature. The first pre-determined temperature is typically the pre-determined liquefaction temperature of the aryl carboxylic acid at which the aryl carboxylic completely, liquefies along with the ionic compound to provide the liquefied composition.

The first pre-determined temperature typically varies between 20° C. to 300° C., preferably above 100° C.

The physical state of the obtained composition to a great extent depends on the temperature and concentration of the aryl carboxylic acids and the ionic compounds used. The liquefied composition obtained in accordance with the process of the present disclosure is in clear solution form.

In addition to forming a liquefied composition, the ionic compound employed in the process of the present disclosure also imparts the role of a solvent suitable enough to dissolve the various intermediate and the side products present in the first mixture along with said aryl carboxylic acids. The process of the present disclosure advantageously uses optimal amounts of ionic compound as compared to prior-art processes wherein ionic compounds are used in bulk quantities as a solvent. Though, the ionic compound in accordance with the process of the present disclosure is used in an optimal amount, it is sufficiently being used as a solvent.

The liquefied composition which is a clear solution in accordance with the process of the present disclosure comprises each of the aryl carboxylic acids and the ionic compound in dissolved form. In addition, the other intermediates and side products present in the first mixture also remain dissolved in the liquefied composition.

The liquefied composition, which is a clear solution, is then subjecting to a second pre-determined temperature to fractionally precipitate an aryl carboxylic acid from the liquefied composition. The second pre-determined temperature is typically the pre-determined precipitation temperature of the aryl carboxylic acid and is considerably lower than the first pre-determined temperature. Therefore, the method step of subjecting the liquefied composition to the second pre-determined temperature is typically a method step of cooling the liquefied composition under controlled temperature conditions to fractionally precipitate an aryl carboxylic acid from the liquefied composition.

The second pre-determined temperature of the liquefied composition plays a very significant role in fractionally crystallizing and precipitating an aryl carboxylic acid from the liquefied composition while leaving remaining aryl carboxylic acids, the intermediate and the side products dissolved in the liquefied composition.

The aryl carboxylic acids, present in the first mixture, dissolve in the ionic compound at considerably higher temperature as compared to the intermediate and the side products dissolve at a considerably lower temperature. Therefore, the inventors of the present disclosure particularly emphasize on adjusting the second pre-determined temperature of the liquefied composition so that each of the aryl carboxylic acids dissolved in the liquefied composition precipitates fractionally one by one.

In accordance with one of the embodiments of the present disclosure, the liquefied composition is subjected to the second pre-determined temperature varying between 30° C. to 200° C., preferably between 80° C. to 120° C. to fractionally crystallize and precipitate an aryl carboxylic acid.

The process of the present disclosure further comprises the method steps of separating the precipitated aryl carboxylic acid, washing and drying the isolated aryl carboxylic acid to obtain said aryl carboxylic acid in pure form.

The liquefied composition obtained in accordance with the process of the present disclosure is subjected to vacuum filtration to isolate the precipitated aryl carboxylic acid and to obtain mother liquor. The isolated aryl carboxylic acid is then subjected to a hot water wash to further remove the traces of impurity. The separated and washed aryl carboxylic acid is then dried at 100° C. for 3 hours to obtain aryl carboxylic acid in pure form.

The mother liquor obtained in accordance with the process of the present disclosure is further subjected to a second pre-determined temperature to fractionally precipitate the remaining aryl carboxylic acids from the liquefied composition. The method step of subjecting the mother liquor to a second pre-determined temperature is iterated until each of the remaining aryl carboxylic acids fractionally precipitates one by one from the mother liquor.

The fractionally precipitated each of the aryl carboxylic acids is isolated separately from each other, washed and dried further as described above to obtain each aryl carboxylic acids in pure form.

The mother liquor obtained after iterated method steps of subjecting to the second pre-determined temperature remains in liquefied form that comprises the ionic compound, the intermediate and the side products in dissolved form.

The process of the present disclosure further comprising a method step of adding at least one solvent; the solvent may be added either during the method step of subjecting the resultant mixture to the first pre-determined temperature or during the method step of subjecting the liquefied composition to the second pre-determined temperature or during both. In accordance with one of the preferred embodiment of the present disclosure, the solvent is added during both the method step of subjecting the resultant mixture at the first pre-determined temperature and the method step of subjecting the liquefied composition to the second pre-determined temperature.

Typically, the total amount of solvent added during both method steps varies between 25 and 0.0001 w/v.

The solvent suitable for the purpose of the present disclosure is miscible with at least one of the first mixture, the ionic compound and the resultant mixture. The solvent suitable for the purpose of the present disclosure is at least one selected from the group of solvents consisting of water, aliphatic alcohols, aromatic alcohols and carboxylic acids. The preferred solvent is selected from the group of solvents consisting of water, aliphatic alcohols and aromatic alcohols.

Preferably, the solvent is at least one selected from the group consisting of benzyl alcohol, phenethyl alcohol, phenyl propyl alcohol, n-octanol, benzaldehyde, benzyl acetate, cetyl alcohol, fatty alcohols, phenol, substituted phenols, $C_8$-$C_{20}$ alcohols and substituted benzyl alcohols including, but are not limited to, 2-methylbenzyl alcohol, 4-chloro-2methylbenzyl alcohol, 5-fluoro-2-methylbenzyl alcohol, o-fluorobenzyl alcohol; o-chlorobenzyl alcohol, o-bromobenzyl alcohol, o-iodobenzyl alcohol and o-nitrobenzyl alcohol.

The particularly preferred solvent for the purpose of the present disclosure is benzyl alcohol. The presence of miscible solvent in the process of the present disclosure further aids in keeping the intermediate products, particularly 4-carbxobenzaldehyde in completely dissolved form in the mother liquor.

The pure aryl carboxylic acids obtained in accordance with the process of the present disclosure are individually analyzed using dropping mercury polarography for analyzing the contents of various intermediates products.

The process for separating aryl carboxylic acids in accordance with the present disclosure reduces at least one intermediate product, said intermediate product is 4-carboxybenzaldehyde. The amount of the 4-carboxybenzaldehyde in the separated aryl carboxylic acids is typically reduced by 25% to 99.9% as compared to its amount in the first mixture.

The process of the present disclosure provides a very simple and efficient method for separating aryl carboxylic acids using ionic compound. Also the ionic compound of the present disclosure is used as solvents for dissolution of various intermediate and side product present in the first mixture.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form part of the prior art base or were common general knowledge in the field relevant to the disclosure as it existed anywhere before the priority date of this application.

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

EXAMPLE 1

2.8 grams of choline chloride was mixed with 1.66 grams of terephthalic acid in 2:1 mole ratio and temperature was raised up to 224° C. A composition, which is a clear solution, was obtained. Terephthalic acid was recrystallized on cooling the composition. The recrystallized terephthalic acid was separated by vacuum filtration, washed with hot water and further subjected to vacuum filtration to obtain purified solid of terephthalic acid.

EXAMPLE 2

1.39 grams of choline chloride was mixed with 1.5 grams of 4-carboxybenzaldehyde in 1:1 mole ratio and temperature was raised up to 160° C. A composition was obtained which is a clear solution.

EXAMPLE 3

1.39 grams of choline chloride was mixed with 1.36 grams of para-toluic acid in 1:1 mole ratio and temperature was raised up to 150° C. A composition was obtained which is a clear solution.

EXAMPLE 4

2.8 grams of choline chloride was mixed with 1.66 grams of isophthalic acid in 2:1 mole ratio and temperature was raised up to 170° C. A composition, which is a clear solution, was obtained.

EXAMPLE 5

1.39 grams of choline chloride was mixed with 1.22 grams of benzoic acid in 1:1 mole ratio and temperature was raised up to 80° C. A composition was obtained which is a clear solution.

EXAMPLE 6

4.2 grams of choline chloride was mixed with 2.1 grams of trimellitic acid in 3:1 mole ratio and temperature was raised up to 180° C. A composition was obtained which is turbid in nature.

EXAMPLE 7

2.8 grams of choline chloride was mixed with 2.42 grams of diphenic acid in 2:1 mole ratio and temperature was raised up to 100° C. A composition was obtained which is a clear solution.

While comparing examples 1-7, it is clearly evident that terephthalic acid dissolves in ionic compound at a considerably higher temperature as compared to the intermediate products, for example, 4-carboxybenzaldehyde, para-toluic acid, isophthalic acid, benzoic acid and the like. Therefore, a temperature range is to be chosen at which only terephthalic acid crystallizes and precipitates while intermediate products remain dissolved in the clear solution.

Similar to the procedure of examples 1 to 7, solubility of terephthalic acid and intermediate products in 1-butyl-3-methyl imidazolium chloride ionic compound is determined in the following examples 8-14.

EXAMPLE 8

3.49 grams of 1-butyl-3-methyl imidazolium chloride was mixed with 1.66 grams of terephthalic acid in 2:1 mole ratio and temperature was raised up to 160° C. A composition was obtained which is a clear solution.

EXAMPLE 9

1.75 grams of 1-butyl-3-methyl imidazolium chloride was mixed with 1.5 grams 4-carboxybenzaldehyde in 1:1 mole ratio and temperature was raised up to 86° C. A composition was obtained which is a clear solution.

EXAMPLE 10

1.75 grams of 1-butyl-3-methyl imidazolium chloride was mixed with 1.36 grams of para-toluic acid in 1:1 mole ratio and temperature was raised up to 50° C. A composition was obtained which is a clear solution.

EXAMPLE 11

3.49 grams of 1-butyl-3-methyl imidazolium chloride was mixed with 1.66 grams of isophthalic acid in 2:1 mole ratio and temperature was raised up to 90° C. A composition was obtained which is a clear solution.

EXAMPLE 12

1.75 grams of 1-butyl-3-methyl imidazolium chloride was mixed with 1.22 grams of benzoic acid in 1:1 mole ratio. At 27° C., a composition was obtained which is a clear solution.

EXAMPLE 13

5.2 grams of 1-butyl-3-methyl imidazolium chloride was mixed with 2.1 grams of trimellitic acid in 3:1 mole ratio and temperature was raised up to 100° C. A composition was obtained which is a clear solution.

EXAMPLE 14

3.49 grams of 1-butyl-3-methyl imidazolium chloride was mixed with 2.42 grams of diphenic acid in 2:1 mole ratio and temperature was raised up to 100° C. A composition was obtained which is a clear solution.

Similar to the examples 1-7, examples 8-14 also clearly indicate that terephthalic acid dissolves at considerably higher temperature (160° C.) as compared to intermediates dissolving at lower temperature i.e. from 27° C. to 100° C.

EXAMPLE 15

1.99 grams of choline mesylate was mixed with 1.5 grams of 4-carboxy benzaldehyde in 1:1 mole ratio and temperature was raised up to 175° C. A composition was obtained which is a clear solution.

EXAMPLE 16

1.99 grams of choline mesylate was mixed with 1.36 grams of para-toluic acid in 1:1 mole ratio and temperature was raised up to 140° C. A composition was obtained which is a clear solution.

EXAMPLE 17

1.99 grams of choline mesylate was mixed with 1.22 grams of benzoic acid in 1:1 mole ratio and temperature was raised up to 65° C. A composition was obtained which is a clear solution.

EXAMPLE 18

0.07 grams of 4-carboxybenzaldehyde was mixed with 4.6 grams of 1-Butyl-3-methyl imidazoliummesyl at 60° C. and a clear solution was obtained. 4-carboxybenzaldehyde remained in solution form even after cooling the solution to room temperature.

EXAMPLE 19

0.2 grams of terephthalic acid was mixed with 3.2 grams of trihexyltetradecylphosphonium bromide at 160° C. and a clear solution was obtained.

EXAMPLE 20

Example 12 was repeated and water was added to ionic compound to crystallize the benzoic acid.

EXAMPLE 21

3.68 grams of choline bromide was mixed with 1.66 grams of terephthalic acid in 2:1 mole ratio and temperature was raised up to 220° C. A composition was obtained which is a clear solution.

EXAMPLE 22

1.84 grams of choline bromide was mixed with 1.5 grams of 4-carboxybenzaldehyde in 1:1 mole ratio and temperature was raised up to 185° C. A composition was obtained which is a clear solution.

EXAMPLE 23

1.84 grams of choline bromide was mixed with 1.36 grams of para-toluic acid in 1:1 mole ratio and temperature was raised up to 170° C. A composition was obtained which is a clear solution.

EXAMPLE 24

1.84 grams of choline bromide was mixed with 1.22 grams of benzoic acid in 1:1 mole ratio and temperature was raised up to 90° C. A composition was obtained which is a clear solution.

EXAMPLE 25

4.38 grams of 1-butyl-3-methyl imidazolium bromide was mixed with 1.66 grams of terephthalic acid in 2:1 mole ratio and temperature was raised up to 180° C. A composition was obtained which is a clear solution.

EXAMPLE 26

2.19 grams of 1-butyl-3-methyl imidazolium bromide was mixed with 1.5 grams of 4-carboxybenzaldehyde in 1:1 mole ratio and temperature was raised up to 135° C. A composition was obtained which is a clear solution.

EXAMPLE 27

2.19 grams of 1-butyl-3-methyl imidazolium bromide was mixed with 1.36 grams of para-toluic acid in 1:1 mole ratio and temperature was raised up to 90° C. A composition was obtained which is a clear solution.

EXAMPLE 28

2.19 grams of 1-butyl-3-methyl imidazolium bromide was mixed with 1.22 grams of benzoic acid in 1:1 mole ratio and temperature was raised up to 30° C. A composition was obtained which is a clear solution.

EXAMPLE 29

This example describes a process for the purification of crude terephthalic acid in accordance with the present disclosure:

1.5 grams of crude terephthalic acid was mixed with 6.67 grams of 1-butyl-3-methyl imidazolium chloride at 120° C. and atmospheric pressure in a 100 ml round bottom flask. 25 grams of benzyl alcohol at 80° C. was added to reconstitute terephthalic acid from this mixture. The reconstituted solid was then separated by vacuum filtration and was subjected to a hot water wash followed by vacuum filtration to separate purified solid terephthalic acid. The obtained pure terephthalic acid was then dried at 100° C. for 3 hours. Dried purified solid sample was further analyzed using dropping mercury polarography for 4-carboxybenzaldehyde content. The result is provided in table-1.

EXAMPLE 30

The purification of crude terephthalic acid was conducted in accordance with the process of Example 29 except water was used as a reconstituted solvent. The obtained result is illustrated in Table-1.

EXAMPLE 31

Pure terephthalic acid was obtained in a similar manner as in example-29 except acetic acid was used as a reconstitution solvent. The obtained result was summarized in Table-1.

EXAMPLE 32

The procedure of example-29 was repeated using N-methyl-2-pyrrolidone as a reconstitution solvent. The obtained result was given in Table-1.

TABLE 1

Purification of crude terephthalic acid using 1-butyl-3methylimidazolium chloride as an ionic compound.

| Example | Ionic Compound | Reconstitution solvent | Temp (°C.) | 4-carboxybenzaldehyde content (ppm) Initial | 4-carboxybenzaldehyde content (ppm) Final | 4-carboxybenzaldehyde % reduction |
|---|---|---|---|---|---|---|
| 29 | 1-butyl-3-methylimidazolium chloride | Benzyl alcohol | 120° C. | 3270 | 2070 | 36.7 |
| 30 | | Water | | | 2950 | 9.7 |
| 31 | | Acetic acid | | | 2520 | 22.7 |
| 32 | | N-methyl-2-pyrrolidone | | | 3070 | 6.0 |

EXAMPLE 33

The purification of crude terephthalic acid was conducted in a similar manner as in Example 29 except 8.55 grams of 1-butyl-3-methyl imidazolium methanesulfonate was used instead of 1-butyl-3-methylimidazolium chloride. The obtained result was illustrated in Table-2.

EXAMPLE 34

The purification of crude terephthalic acid was conducted in a similar manner as in Example 33 except water was used as a reconstitution solvent. The obtained result was given in Table-2.

EXAMPLE 35

Pure terephthalic acid was obtained in a similar manner as in example-33 except acetic acid was used as a reconstitution solvent. The obtained result was summarized in Table-2.

EXAMPLE 36

The procedure of example-33 was repeated using N-methyl-2-pyrrolidone as a reconstitution solvent. The obtained result was given in Table-2.

TABLE 2

Purification of crude terephthalic acid using 1-butyl-3methylimidazolium methanesulfonate as ionic compound.

| Example | Ionic Compound | Reconstitution solvent | Temp (°C.) | 4-carboxybenzaldehyde content (ppm) Initial | 4-carboxybenzaldehyde content (ppm) Final | 4-carboxybenzaldehyde % reduction |
|---|---|---|---|---|---|---|
| 33 | 1-butyl-3-methylimidazolium methanesulfonate | Benzyl alcohol | 120° C. | 3270 | 1717 | 47.5 |
| 34 | | Water | | | 3238 | 1.0 |
| 35 | | Acetic acid | | | 2780 | 15.0 |
| 36 | | N-methyl-2-pyrrolidone | | | 3099 | 5.25 |

EXAMPLE 37

2.0 grams of crude terephthalic acid was mixed with 8.56 grams of 1-butyl-3-methyl imidazolium chloride at 160° C. and atmospheric pressure. The temperature of the obtained mixture was then lowered to 120° C. 25 grams of benzyl alcohol at 80° C. was added to the mixture and stirred for 10 minutes. Terephthalic acid was recrystallized as soon as benzyl alcohol was added to it. The solid was filtered under vacuum and washed with hot water at 80° C. The above described procedure was repeated two times more. A sample of pure terephthalic acid as obtained after every stage of purification was dried at 100° C. for 3 hours. The obtained pure samples were analyzed using dropping mercury polarography for 4-carboxybenzaldehyde content and the results were given in Table-3.

TABLE 3

3-Stage purification of crude terephthalic acid using benzyl alcohol as reconstitution solvent.

| Stage | Ionic Compound | Reconstitution solvent | Temp (° C.) | 4-carboxybenzaldehyde content (ppm) Initial | Final | 4-carboxybenzaldehyde % reduction |
|---|---|---|---|---|---|---|
| 1 | 1-butyl-3-methylimidazolium | Benzyl alcohol | 160° C. | 3270 | 1795 | 45.0 |
| 2 | chloride | | | | 1230 | 62.4 |
| 3 | | | | | 857 | 73.8 |

EXAMPLE 38

Procedure of Example-37 was repeated using acetic acid as a reconstitution solvent and result was given in Table-4.

TABLE 4

3-Stage purification of crude terephthalic acid using acetic acid as a reconstitution solvent.

| Stage | Ionic Compound | Reconstitution solvent | Temp (° C.) | 4-carboxybenzaldehyde content (ppm) Initial | Final | 4-carboxybenzaldehyde % reduction |
|---|---|---|---|---|---|---|
| 1 | 1-butyl-3-methylimidazolium | Acetic Acid | 160° C. | 3270 | 2022 | 38.15 |
| 2 | chloride | | | | 1695 | 48.15 |
| 3 | | | | | 1453 | 55.56 |

EXAMPLE 39

Procedure of Example-37 was repeated using n-octanol as a reconstitution solvent and the result was given in Table-5.

TABLE 5

3-Stage purification of crude terephthalic acid using n-octanol as a reconstitution solvent.

| Stage | Ionic Compound | Reconstitution solvent | Temp (° C.) | 4-carboxybenzaldehyde content (ppm) Initial | Final | 4-carboxybenzaldehyde % reduction |
|---|---|---|---|---|---|---|
| 1 | 1-butyl-3-methylimidazolium | n-octanol | 160° C. | 3270 | 3021 | 7.6 |
| 2 | chloride | | | | 2875 | 12.07 |
| 3 | | | | | 2739 | 16.23 |

Technical Advancement:

The present disclosure relates to a process for separating aryl carboxylic acids from a mixture comprising a plurality of aryl carboxylic acids, has the following technical advancement:
- Employing ionic compound for the separation of aryl carboxylic acids, and
- Employing optimal amount of ionic compound for the separation of aryl carboxylic acids as compared to the prior-art processes wherein ionic compounds are usually employed in bulk quantities.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the particular features of this disclosure, it will be appreciated that various modifications can be made, and that many changes can be made in the preferred embodiment without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

The invention claimed is:

1. A process for separating aryl carboxylic acids from a mixture comprising a plurality of aryl carboxylic acids, said process comprising the following steps:
   i. providing a first mixture comprising at least two aryl carboxylic acids, each of said aryl carboxylic acids having a pre-determined liquefaction temperature and a pre-determined precipitation temperature;
   ii. admixing said first mixture with an ionic compound; wherein the molar ratio of the ionic compound and the first reaction mixture is in the range of 1:1 to 6:1, to obtain a resultant mixture;

iii. subjecting the resultant mixture to a first pre-determined temperature until the first mixture completely liquefies along with the ionic compound to obtain a liquefied composition;
iv. subjecting the liquefied composition to a second pre-determined temperature, and adding at least one solvent to fractionally precipitate an aryl carboxylic acid, wherein said second pre-determined temperature is lower than the first pre-determined temperature;
v. isolating said precipitated aryl carboxylic acid from the liquefied composition and collecting the mother liquor; and
vi. iterating the method step of subjecting to a second pre-determined temperature to further precipitate each of the remaining aryl carboxylic acids one by one from the mother liquor while retaining the mother liquor in liquefied form.

2. The process as claimed in claim 1, wherein said first pre-determined temperature is the pre-determined liquefaction temperature of the aryl carboxylic acid.

3. The process as claimed in claim 1, wherein said second pre-determined temperature is the pre-determined precipitation temperature of the aryl carboxylic acid.

4. The process as claimed in claim 1, wherein the first pre-determined temperature is in the range of 20° C. to 300° C. and the second pre-determined temperature is in the range of 30° C. to 200° C.

5. The process as claimed in claim 1, wherein said first mixture comprises at least two of said aryl carboxylic acids in a total amount varying between 50 to 99.999% by weight, with respect to the total weight of the first mixture.

6. The process as claimed in claim 1, wherein at least two of said aryl carboxylic acids are selected from the group consisting of terephthalic acid, isophthalic acid, orthophthalic acid, benzoic acid, p-toluic acid, m-toluic acid, o-toluic acid, 4-formyl benzoic acid, 3-formyl benzoic acid, 2-formyl benzoic acid, Naphthenic acid, Naphthoic acid, Trimesic acid, 3-Bromo-4-methyl benzoic acid, 3-Hydroxy-4-methyl benzoic acid, Trimellitic acid, mellitic acid, 4-methyl phthalic acid, 2-Biphenyl corboxylic acid, Hemimellitic acid, 4-Bromo-methyl benzoic acid and substituted benzoic acid.

7. The process as claimed in claim 1, wherein said first mixture further comprises at least one intermediate product selected from the group consisting of 4-carboxybenzaldehyde, para-toluic acid and para-tolualdehyde.

8. The process as claimed in claim 1, wherein said first mixture comprises terephthalic acid and 4-carboxybenzaldehyde.

9. The process as claimed in claim 7, wherein said at least one intermediate product is 4-carboxybenzaldehyde present in an amount ranging between 0.001% and 50% by weight, with respect to the total weight of the first mixture.

10. The process as claimed in claim 1, wherein the ionic compound is at least one selected from the group of ionic compounds consisting of choline chloride, choline bromide, choline acetate, choline methane sulfonate, choline mesylate, 1-butyl-3-methyl imidazolium chloride, 1-butyl-3-methyl imidazolium bromide, 1-butyl-3-methyl imidazolium acetate, 1-butyl-3-methyl imidazolium methane sulfonate, 1-butyl-3-methyl imidazolium phosphate, 1-ethyl-3-methyl imidazolium chloride, 1-ethyl-3-methyl imidazolium bromide, 1-ethyl-3-methyl imidazolium acetate, 1-ethyl-3-methyl imidazolium methane sulfonate, 1-ethyl-3-methyl imidazolium phosphate, 1-benzyl-3-methyl imidazolium chloride, 1-benzyl-3-methyl imidazolium bromide, 1-benzyl -3-methyl imidazolium acetate, 1-benzyl-3-methyl imidazolium methane sulfonate, 1-benzyl-3-methyl imidazolium phosphate, Tetrabutyl phosphonium chloride, Tetrabutyl phosphonium bromide, Tetrabutyl phosphonium acetate, Tetrabutyl phosphonium methane sulfonate, Tetrabutyl phosphonium phosphate, Trihexyl Tetradecyl phosphonium chloride, Trihexyl Tetradecyl phosphonium bromide, Trihexyl Tetradecyl phosphonium acetate, Trihexyl Tetradecyl phosphonium decanoate, Benzyl tributyl phosphonium bromide, Tetrabutyl ammonium chloride, Tetrabutyl ammonium bromide, Tetrabutyl ammonium acetate, Tetrabutyl ammonium methane sulfonate, Tetrabutyl ammonium phosphate and Benzyl tributyl ammonium bromide.

11. The process as claimed in claim 1, wherein the weight proportion of the ionic compound and the first mixture, expressed in terms of mole ratio, is 1:1.

12. The process as claimed in claim 1, wherein said solvent is miscible with at least one of said first mixture, said ionic compound and said resultant mixture.

13. The process as claimed in claim 1, wherein said solvent is at least one solvent selected from the group of solvents consisting of water, aliphatic alcohols, aromatic alcohols and carboxylic acids.

14. The process as claimed in claim 1, wherein the solvent is at least one solvent selected from the group of solvents consisting of benzyl alcohol, substituted benzyl alcohol, phenethyl alcohol, phenyl propyl alcohol, n-octanol, benzaldehyde, benzyl acetate, cetyl alcohol, fatty alcohols, phenol, substituted phenols and $C_8$-$C_{20}$ alcohols.

15. The process as claimed in claim 1, wherein the solvent is at least one substituted benzyl alcohol selected from the group consisting of 2-methylbenzyl alcohol, 4-chloro-2-methylbenzyl alcohol, 5-fluoro-2-methylbenzyl alcohol, o-fluorobenzyl alcohol, o-chlorobenzyl alcohol, o-bromobenzyl alcohol, o-iodobenzyl alcohol and o-nitrobenzyl alcohol.

16. The process as claimed in claim 1, wherein said solvent is benzyl alcohol.

17. The process as claimed in claim 1, wherein said solvent is added during the method step (iv) in a total amount varying between 25 to 0.0001 w/v.

18. The process as claimed in claim 1, wherein said mother liquor comprises 4-carboxybenzaldehyde in completely dissolved form in the presence of said at least one miscible solvent.

19. The process as claimed in claim 1, wherein the amount of 4-carboxybenzaldehyde in said precipitated aryl carboxylic acid is reduced in the range of 25% to 99.9%, with respect to its amount in the first mixture.

* * * * *